(12) United States Patent
Escalona et al.

(10) Patent No.: US 11,116,630 B2
(45) Date of Patent: Sep. 14, 2021

(54) SHEATHING AID

(71) Applicant: BOSTON SCIENTIFIC SCIMED, INC., Maple Grove, MN (US)

(72) Inventors: Floriza Q. Escalona, San Jose, CA (US); Takashi H. Ino, San Jose, CA (US); Mimi Trinh Fitterer, Belmont, CA (US); Andrew J. H. Backus, Santa Cruz, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 314 days.

(21) Appl. No.: 15/498,758

(22) Filed: Apr. 27, 2017

(65) Prior Publication Data

US 2017/0325951 A1 Nov. 16, 2017

Related U.S. Application Data

(60) Provisional application No. 62/336,953, filed on May 16, 2016.

(51) Int. Cl.
*A61F 2/24* (2006.01)
*A61F 2/966* (2013.01)
*A61F 2/95* (2013.01)

(52) U.S. Cl.
CPC ............ *A61F 2/2436* (2013.01); *A61F 2/243* (2013.01); *A61F 2/2418* (2013.01);
(Continued)

(58) Field of Classification Search
CPC ...... A61F 2/2436; A61F 2/966; A61F 2/2418; A61F 2/2466; A61F 2/2442; A61F 2/243;
(Continued)

(56) References Cited

U.S. PATENT DOCUMENTS 5,320,605 A * 6/1994 Sahota ................ A61M 25/104
604/101.01
8,052,749 B2 11/2011 Salahieh et al.
(Continued)

FOREIGN PATENT DOCUMENTS

CN 1905846 A 1/2007
EP 2205184 B1 2/2012
(Continued)

OTHER PUBLICATIONS

US 8,062,357 B2, 11/2011, Salahieh et al. (withdrawn)
International Search Report and Written Opinion dated Jul. 24, 2017 for International Application No. PCT/US2017/032049.

*Primary Examiner* — Wade Miles
*Assistant Examiner* — Michael G Mendoza
(74) *Attorney, Agent, or Firm* — Seager, Tufte & Wickhem LLP

(57) ABSTRACT

A medical device apparatus may include a medical implant including a braided anchor member configured to actuate between a delivery configuration and a deployed configuration operatively connected to a delivery system. The delivery system may include a handle, an outer sheath extending distally from the handle, and an inner catheter disposed within the outer sheath. A sheathing aid may connect the delivery system to the medical implant, the sheathing aid being configured to guide the medical implant into the outer sheath upon relative closing movement therebetween. The sheathing aid may include a plurality of arms extending from the inner catheter to a proximal end of the braided anchor member. At least one arm of the plurality of arms may comprise a core member having a width and a flexible member positioned about the core member.

7 Claims, 12 Drawing Sheets

(52) U.S. Cl.
CPC .......... *A61F 2/2442* (2013.01); *A61F 2/2466* (2013.01); *A61F 2/966* (2013.01); *A61F 2/2439* (2013.01); *A61F 2/9522* (2020.05); *A61F 2002/9665* (2013.01); *A61F 2250/0069* (2013.01)

(58) Field of Classification Search
CPC ...... A61F 2002/9665; A61F 2002/9522; A61F 2/2439; A61F 2250/0069
See application file for complete search history.

(56) References Cited

U.S. PATENT DOCUMENTS

| | | |
|---|---|---|
| 8,157,852 B2 | 4/2012 | Bloom et al. |
| 8,157,853 B2 | 4/2012 | Laske et al. |
| 8,828,078 B2 | 9/2014 | Salahieh et al. |
| 9,155,619 B2 | 10/2015 | Liu et al. |
| 9,192,496 B2 | 11/2015 | Robinson |
| 2005/0055077 A1* | 3/2005 | Marco .................. A61M 25/10 623/1.11 |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0283231 A1 | 12/2005 | Haug et al. |
| 2006/0058872 A1 | 3/2006 | Salahieh et al. |
| 2006/0173524 A1 | 8/2006 | Salahieh et al. |
| 2006/0253191 A1 | 11/2006 | Salahieh et al. |
| 2007/0244552 A1 | 10/2007 | Salahieh et al. |
| 2009/0192585 A1 | 7/2009 | Bloom et al. |
| 2009/0198316 A1 | 8/2009 | Laske et al. |
| 2011/0276121 A1 | 11/2011 | Levine |
| 2012/0029627 A1 | 2/2012 | Salahieh et al. |
| 2012/0041550 A1 | 2/2012 | Salahieh et al. |
| 2013/0116770 A1 | 5/2013 | Robinson |
| 2013/0116771 A1 | 5/2013 | Robinson |
| 2013/0116772 A1 | 5/2013 | Robinson |
| 2013/0123897 A1 | 5/2013 | Robinson |
| 2013/0123898 A1 | 5/2013 | Tung et al. |
| 2014/0243967 A1 | 8/2014 | Salahieh et al. |
| 2015/0127094 A1 | 5/2015 | Salahieh et al. |
| 2015/0297378 A1* | 10/2015 | Senness .................. A61F 2/966 623/1.11 |

FOREIGN PATENT DOCUMENTS

| | | |
|---|---|---|
| EP | 2254515 B1 | 1/2015 |
| EP | 2455041 B1 | 7/2015 |
| WO | 2005062980 A2 | 7/2005 |
| WO | 2007053243 A2 | 5/2007 |
| WO | 2009094189 A1 | 7/2009 |
| WO | 2010042950 A2 | 4/2010 |
| WO | 2013066883 A1 | 5/2013 |

* cited by examiner

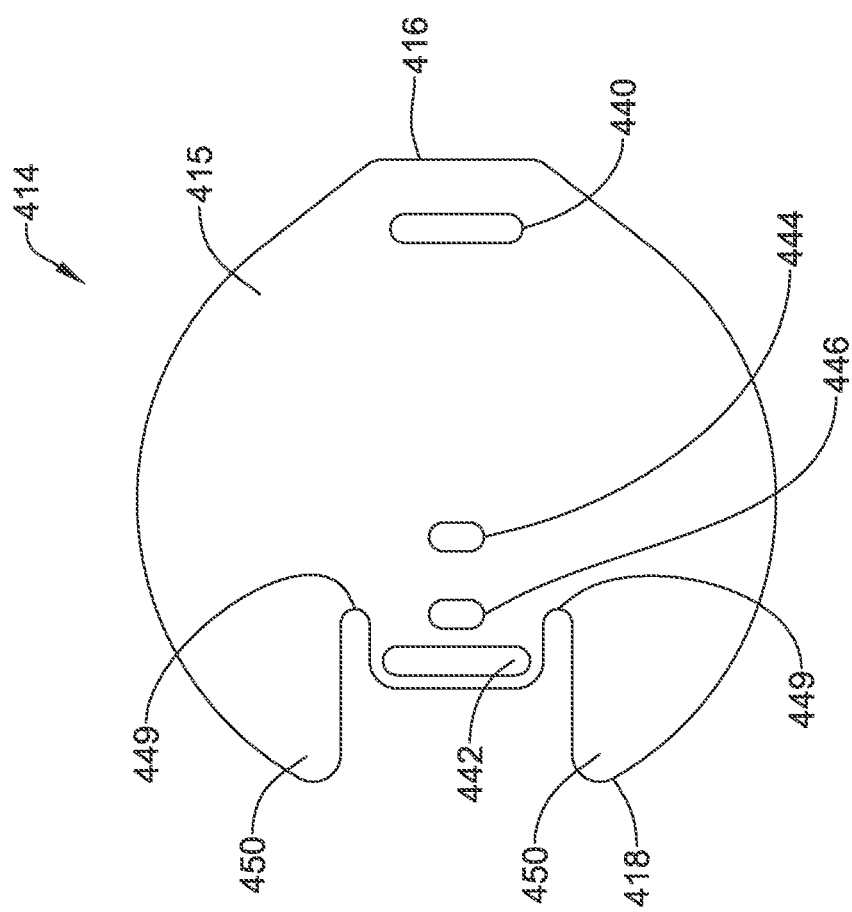

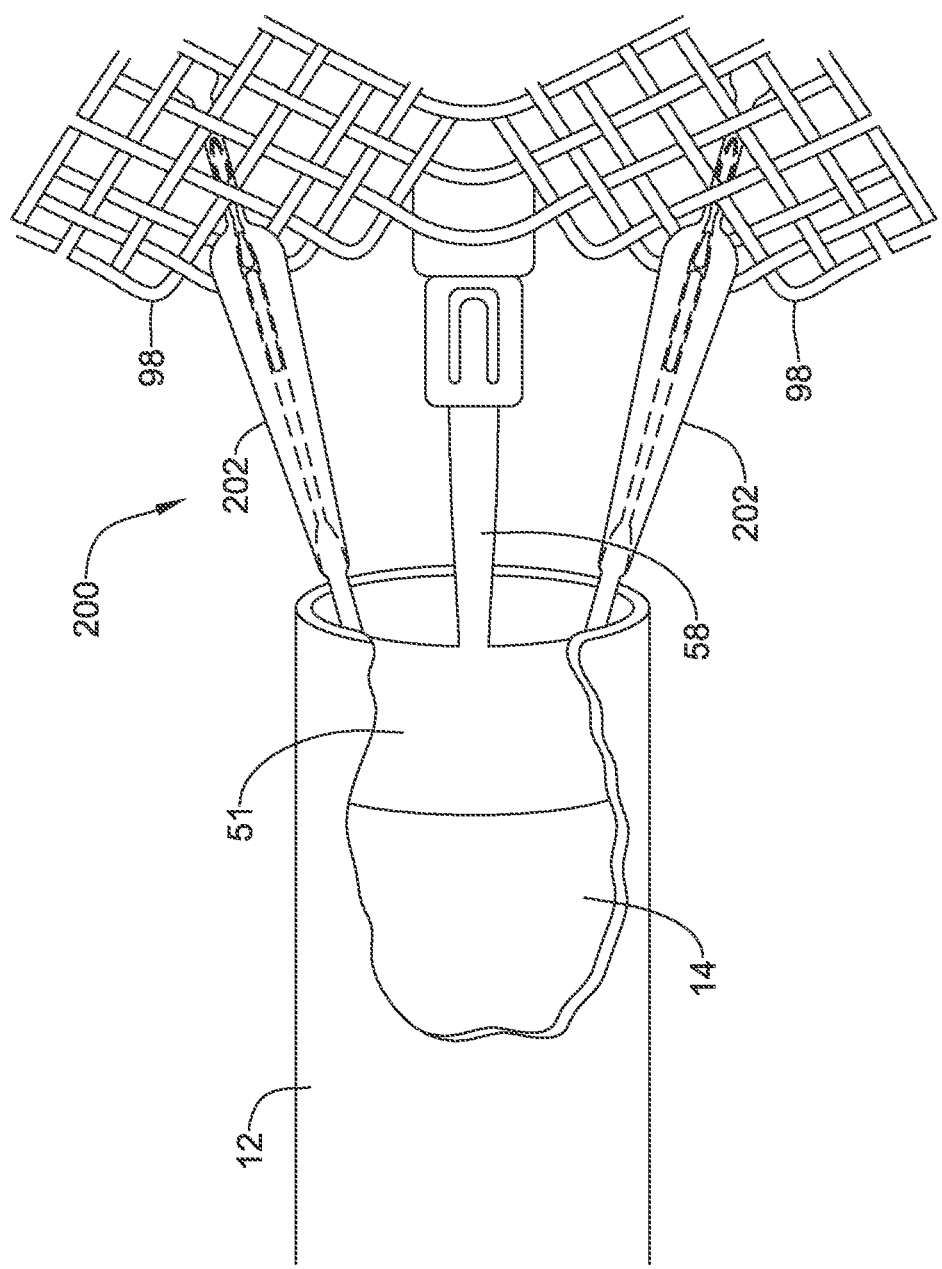

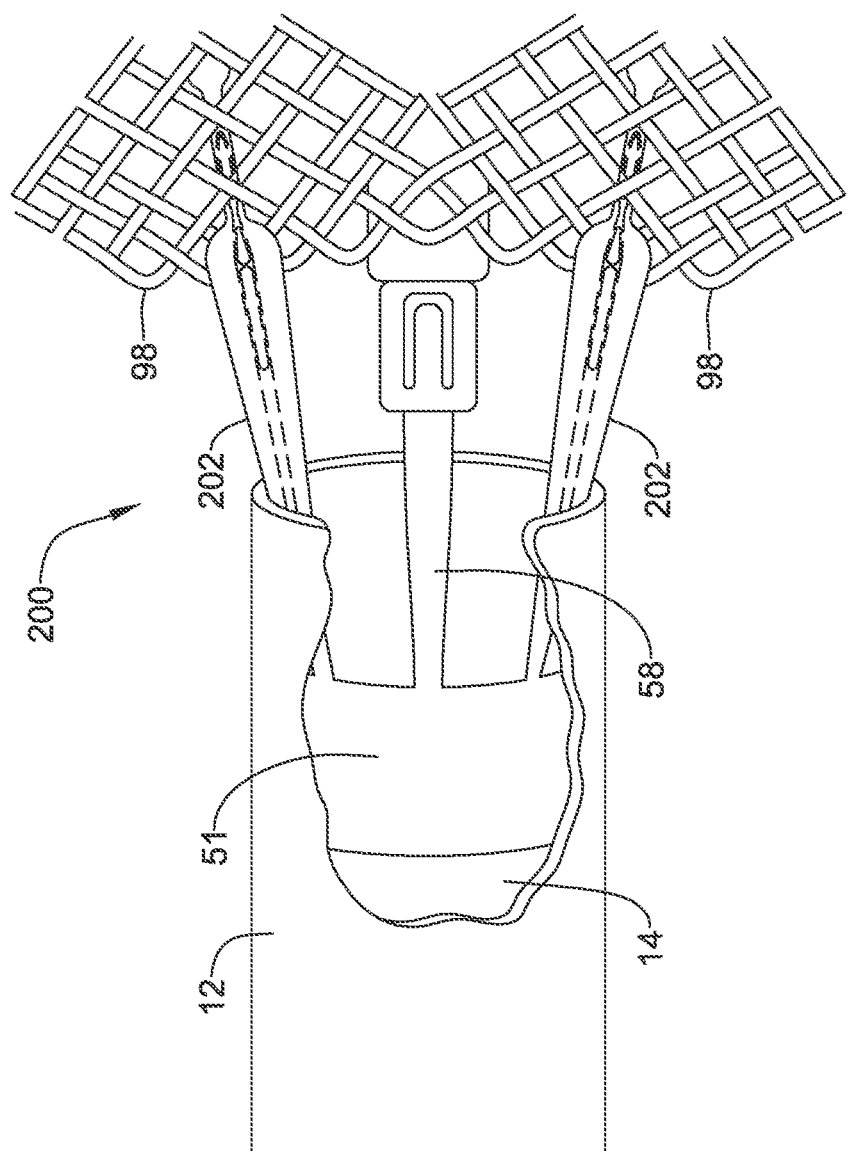

SHEATHING AID

RELATED APPLICATIONS

This application claims priority to U.S. Provisional Application No. 62/336,953, filed May 16, 2016.

TECHNICAL FIELD

The present disclosure pertains to medical devices, and methods for manufacturing and/or using medical devices. More particularly, the present disclosure pertains to sheathing aids for a medical device and/or a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices.

In a first example, a medical device apparatus may comprise a medical implant including a braided anchor member, the braided anchor operatively connected to a delivery system. The delivery system may include a handle, an outer sheath extending distally from the handle, and an inner catheter disposed within the outer sheath. A sheathing aid may connect the delivery system to the medical implant. The sheathing aid may be configured to guide the medical implant into the outer sheath upon relative closing movement therebetween. The sheathing aid may include a plurality of arms extending from the inner catheter to a proximal end of the braided anchor member. At least one arm of the plurality of arms may include a flexible member.

Alternatively or additionally to any of the examples above, in another example, the at least one arm may comprise a core member having a width and the flexible member is positioned about at least a portion of the core member.

Alternatively or additionally to any of the examples above, in another example, the flexible member may comprise a proximal region, an intermediate region and a distal region, the flexible member and may extend along a length of the core member.

Alternatively or additionally to any of the examples above, in another example, a distal end of the flexible member may extend distally beyond a distal end of the core member.

Alternatively or additionally to any of the examples above, in another example, the intermediate region of the flexible member may have a width greater than the width of the core member.

Alternatively or additionally to any of the examples above, in another example, the intermediate region of the flexible member may be positioned over at least a portion of the proximal end of the braided anchor member.

Alternatively or additionally to any of the examples above, in another example, the flexible member may comprise a generally circular pad positioned about an intermediate portion of the core member.

Alternatively or additionally to any of the examples above, in another example, the flexible member may be molded over the core member.

Alternatively or additionally to any of the examples above, in another example, the flexible member may be sutured to the core member.

Alternatively or additionally to any of the examples above, in another example, the flexible member may comprise a first set of apertures configured to receive a suture.

Alternatively or additionally to any of the examples above, in another example, the flexible member may further comprise a second set of apertures configured to receive the core member.

Alternatively or additionally to any of the examples above, in another example, the core member may include a plurality of apertures.

Alternatively or additionally to any of the examples above, in another example, the flexible member may comprise polyether ether ketone (PEEK).

Alternatively or additionally to any of the examples above, in another example, the core member may comprise a metallic material.

Alternatively or additionally to any of the examples above, in another example, the plurality of arms may be configured to releasably engage the braided anchor member.

Alternatively or additionally to any of the examples above, in another example, the braided anchor member may include a plurality of crowns, wherein the flexible member may be configured to be disposed over at least one of the plurality of crowns.

Another example medical device apparatus may comprise a medical implant including a braided anchor member, the braided anchor member operatively connected to a delivery system. The delivery system may include a handle, an outer sheath extending distally from the handle, and an inner catheter disposed within the outer sheath. A sheathing aid may connect the delivery system to the medical implant. The sheathing aid may be configured to guide the medical implant into the outer sheath upon relative closing movement therebetween. The sheathing aid may include a plurality of arms extending from the inner catheter to a proximal end of the braided anchor member. At least one arm of the plurality of arms may include a flexible polymeric member.

Alternatively or additionally to any of the examples above, in another example, the at least one arm may comprise a core member having a width and the flexible member is positioned about at least a portion of the core member.

Alternatively or additionally to any of the examples above, in another example, the flexible member may comprise a proximal region, an intermediate region and a distal region, the flexible member may extend along a length of the core member.

Alternatively or additionally to any of the examples above, in another example, a distal end of the flexible member may extend distally beyond a distal end of the core member.

Alternatively or additionally to any of the examples above, in another example, the intermediate region of the flexible member may have a width greater than the width of the core member.

Alternatively or additionally to any of the examples above, in another example, the intermediate region of the flexible member may be positioned over at least a portion of the proximal end of the braided anchor member.

Alternatively or additionally to any of the examples above, in another example, the flexible member may be molded over the core member.

Alternatively or additionally to any of the examples above, in another example, the flexible member may comprise a generally circular pad positioned about an intermediate portion of the core member.

Alternatively or additionally to any of the examples above, in another example, the flexible member may be sutured to the core member.

Alternatively or additionally to any of the examples above, in another example, the flexible member may comprise a first set of apertures configured to receive a suture.

Alternatively or additionally to any of the examples above, in another example, the flexible member may further comprise a second set of apertures configured to receive the core member.

Alternatively or additionally to any of the examples above, in another example, the core member may include a plurality of apertures.

Alternatively or additionally to any of the examples above, in another example, the plurality of arms may be configured to releasably engage the braided anchor member.

Another example medical device apparatus may comprise a medical implant including a braided anchor member, the braided anchor member operatively connected to a delivery system. The delivery system may include a handle, an outer sheath extending distally from the handle, and an inner catheter disposed within the outer sheath. A sheathing aid may connect the delivery system to the medical implant. The sheathing aid may be configured to guide the medical implant into the outer sheath upon relative closing movement therebetween. The sheathing aid may include a plurality of arms extending from the inner catheter to a proximal end of the braided anchor member. At least one arm of the plurality of arms may comprise a metallic core member having a width and a flexible polymeric member extending along at least a portion of a length of the core member. The flexible member may comprise a proximal region, an enlarged intermediate region and a distal region.

Alternatively or additionally to any of the examples above, in another example, a distal end of the flexible member may extend distally beyond a distal end of the core member.

Alternatively or additionally to any of the examples above, in another example, the intermediate region of the flexible member may have a width greater than the width of the core member.

Alternatively or additionally to any of the examples above, in another example, the braided anchor member may include a plurality of crowns, wherein the enlarged intermediate region of the flexible member may be configured to be disposed over at least one of the plurality of crowns.

Another example medical device apparatus may comprise a medical implant including a braided anchor member operatively connected to a delivery system. The delivery system may include a handle, an outer sheath extending distally from the handle, and an inner catheter disposed within the outer sheath. A sheathing aid may connect the delivery system to the medical implant. The sheathing aid may be configured to guide the medical implant into the outer sheath upon relative closing movement therebetween. The sheathing aid may include a plurality of arms extending from the inner catheter to a proximal end of the braided anchor member. At least one arm of the plurality of arms may comprise a metallic core member having a width and a flexible polymeric pad member disposed over at least a portion of an intermediate region of the core member.

Alternatively or additionally to any of the examples above, in another example, the flexible polymeric pad member may be sutured to the core member.

Alternatively or additionally to any of the examples above, in another example, the flexible polymeric pad member may comprise a first set of apertures configured to receive a suture and a second set of apertures configured to receive the core member.

Alternatively or additionally to any of the examples above, in another example, the braided anchor member may include a plurality of crowns, wherein the flexible polymeric pad member may be configured to be disposed over at least one of the plurality of crowns.

The above summary of some embodiments, aspects, and/or examples is not intended to describe each disclosed embodiment or every implementation of the present disclosure. The FIGS, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 8 illustrates a component of the illustrative arm of FIG. 7;

FIG. 9 illustrates selected components associated with an example medical device system in a deployed configuration prior to sheathing of an example medical implant; and FIG. 10 illustrates selected components associated with an example medical device system in a partially-sheathed configuration during sheathing of an example medical implant.

Figure 1:
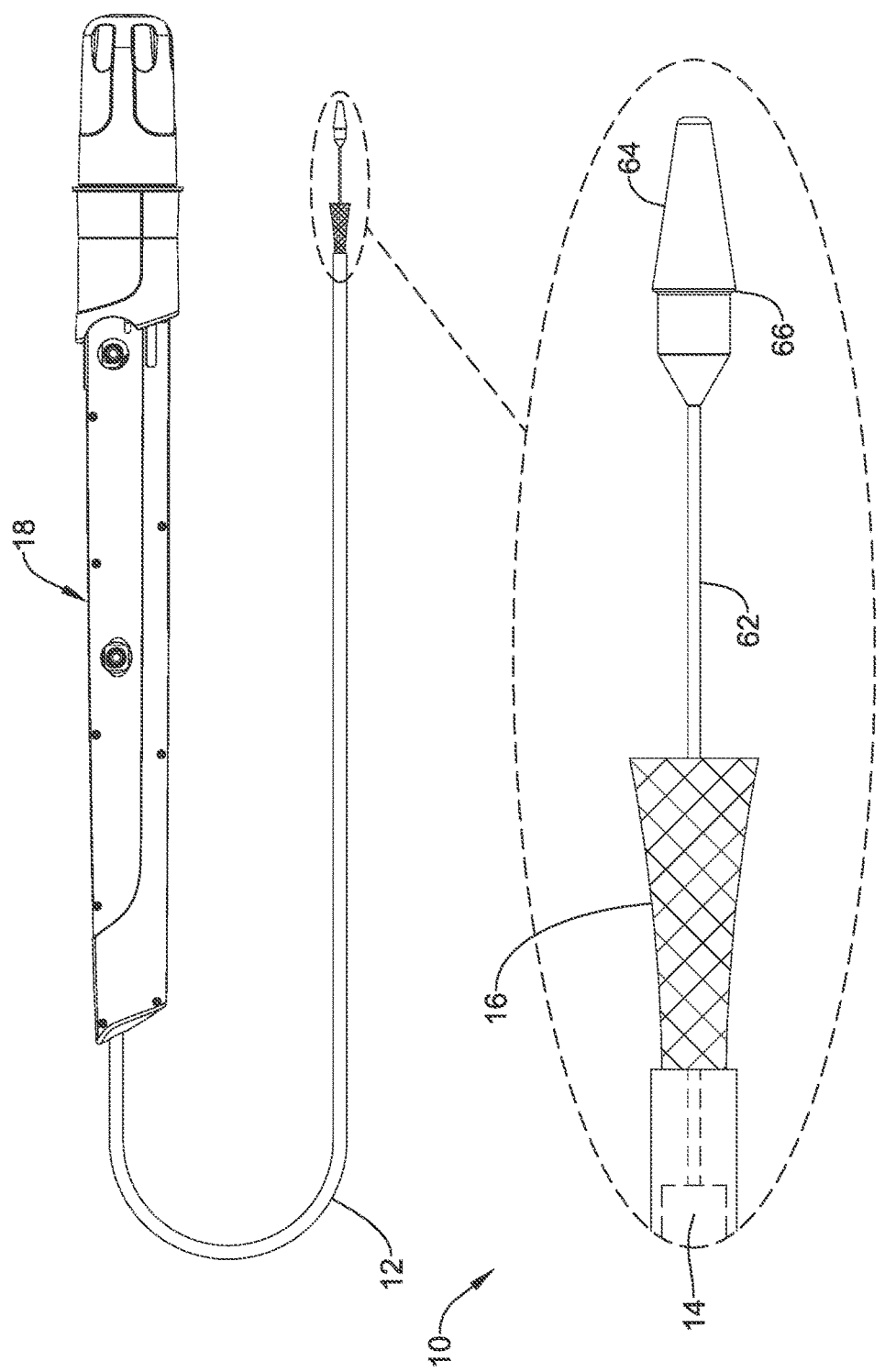
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Generally speaking, in terms of the orientation of the structural elements relative to each other and the operation of the disclosed device(s), a proximal end may be considered closest to the user (or external to a patient) and a distal end farthest from the user (or internal to a patient). However, the skilled artisan will appreciate that the orientations and/or directions may be reversed as necessary or appropriate.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

The medical device system 10, as seen in FIG. 1 for example, may generally be described as a catheter system that includes a delivery system having an outer sheath 12 for a medical implant 16 (e.g., a replacement valve implant, for example, which term may be used interchangeably with the term "medical implant" herein) which may be coupled to the delivery system and disposed within a lumen of the outer sheath 12 during delivery of the medical implant 16. In some embodiments, the delivery system may include an inner catheter 14, as seen in FIG. 2 for example, extending at least partially through the outer sheath 12 (partially seen in phantom in FIG. 1). In some embodiments, the medical implant 16 may be coupled to the inner catheter 14 and disposed within the lumen of the outer sheath 12 during delivery of the medical implant 16. In some embodiments, a handle 18 may be disposed and/or attached at a proximal end of the delivery system, as seen in FIG. 1, and may include one or more actuation means associated therewith. In some embodiments, the handle 18 may be configured to manipulate the position of the outer sheath 12 relative to the inner catheter 14, and/or aid in the deployment of the medical implant 16. In some embodiments, the medical device system 10 may include a nose cone 64 disposed at a distal end of a guidewire extension tube 62, wherein the guidewire extension tube 62 may extend distally from the inner catheter 14. In at least some embodiments, the nose cone 64 may be designed to have an atraumatic shape. In some embodiments, the nose cone 64 may include a ridge or ledge 66 that is configured to abut a distal tip of the outer sheath 12 during delivery of the medical implant 16.

Figure 3:
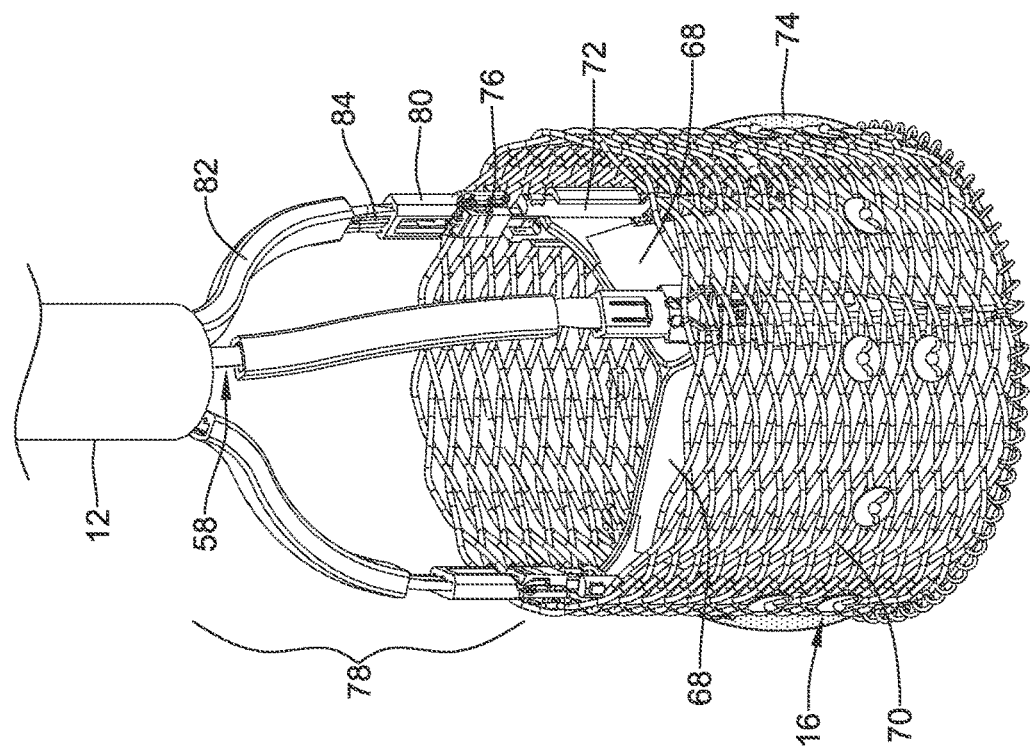
FIG. 3 illustrates an example medical implant associated with an example medical device system.

In use, the medical device system 10 may be advanced percutaneously through the vasculature to a position adjacent to an area of interest or a target location. For example, the medical device system 10 may be advanced through the vasculature and across the aortic arch to a position adjacent to a defective aortic valve. Alternative approaches to treat a defective aortic valve and/or other heart valve(s) are also contemplated with the medical device system 10. During delivery, the medical implant 16 may be generally disposed in an elongated and low profile "delivery" configuration within the delivery system and/or the outer sheath 12 coupled to and/or distal of the inner catheter 14. Once positioned, the outer sheath 12 may be retracted relative to the inner catheter 14, which may be held stationary by the handle 18, and/or the medical implant 16 to expose the medical implant 16. The medical implant 16 may be actuated using the handle 18 in order to translate the medical implant 16 into a generally expanded and larger profile "deployed" configuration suitable for implantation within the anatomy (as seen in FIG. 3, for example). When the medical implant 16 is suitably deployed within the anatomy, the medical implant 16 may be released and/or detached from the medical device system 10, the delivery system can be removed from the vasculature, leaving the medical implant 16 in place in a "released" configuration to function as, for example, a suitable replacement for the native aortic valve. In at least some interventions, the medical implant 16 may be deployed within the native valve (e.g., the native valve is left in place and not excised). Alternatively, the native valve may be removed (such as through valvuloplasty, for example) and the medical implant 16 may be deployed in its place as a replacement.

Figure 2A:
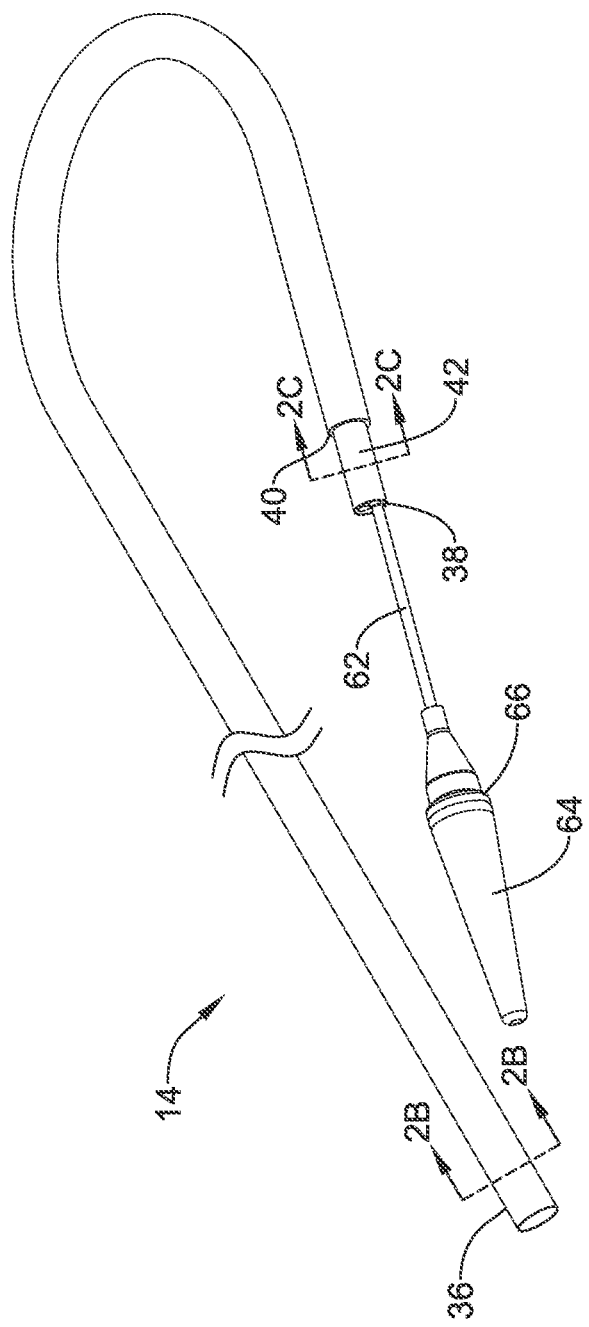
FIG. 2A illustrates a side view of an example inner catheter of FIG. 1.
Figure 2B:
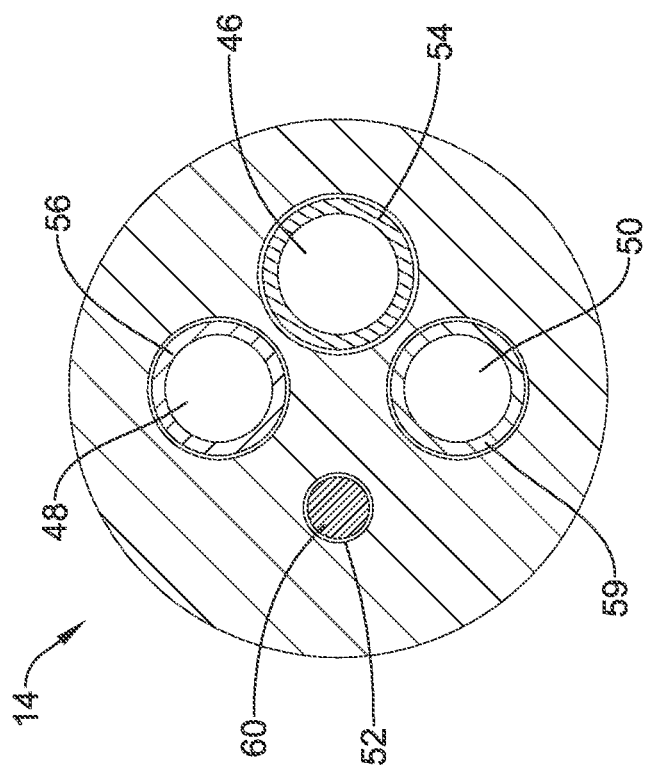
FIG. 2B illustrates a cross-sectional view taken through line 2B-2B in FIG. 2A.
Figure 2C:
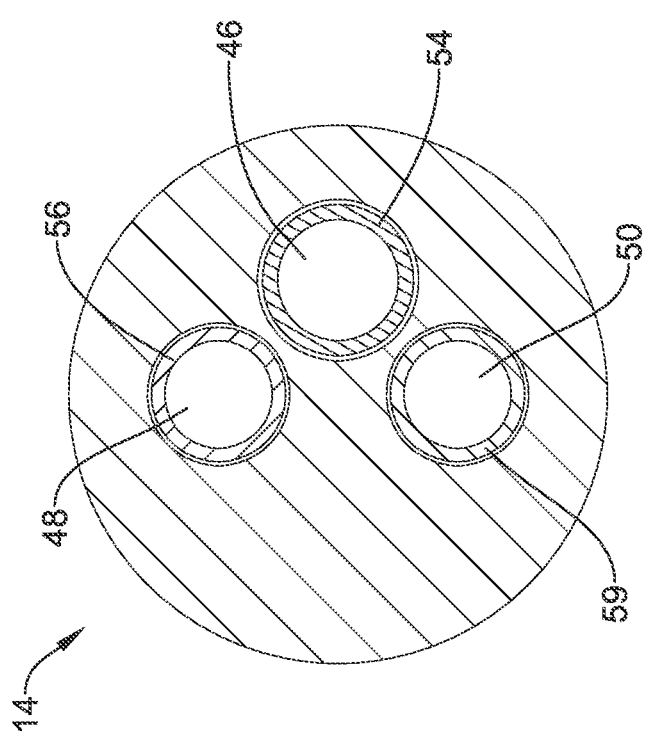
FIG. 2C illustrates a cross-sectional view taken through line 2C-2C in FIG. 2A.

FIG. 2A is a side view of an example inner catheter 14. A distal end region of the inner catheter 14 may include a step in outer diameter 40 that defines a decreased outer diameter section 42. The decreased outer diameter section 42 may define a region where other components of system 10 may be attached. In some embodiments, the inner catheter 14 may include one or more lumens extending therethrough. For example, FIG. 2B (which is a cross sectional view of the inner catheter 14 adjacent to proximal end portion 36 taken at line 2B-2B in FIG. 2A) illustrates that the inner catheter 14 may include a first lumen 46, a second lumen 48, a third lumen 50, and a fourth lumen 52. In general, the lumens 46, 48, 50, 52 may extend along the entire length of inner catheter 14. Other embodiments are contemplated, however, where one or more of the lumens 46, 48, 50, 52 may extend along only a portion of the length of inner catheter 14. For example, the fourth lumen 52 may stop just short of the distal end 38 of inner catheter 14 and/or be filled in at its distal end to effectively end the fourth lumen 52 proximal of the distal end of inner catheter 14, as illustrated in FIG. 2C which is a cross sectional view of the inner catheter 14 adjacent to the distal end 38 taken at line 2C-2C, by the absence of the fourth lumen 52 adjacent to the distal end of inner catheter 14.

In some embodiments, the inner catheter 14 may include an extruded, multi-lumen polymeric shaft. Other forms are also contemplated including other polymer shafts or tubes, metallic shafts or tubes, reinforced shafts or tubes, or the like including other suitable materials such as those disclosed herein. In some embodiments, the inner catheter 14 may be a singular monolithic or unitary member. In some embodiments, the inner catheter 14 may include a plurality of portions or segments that are coupled together. The total length of the inner catheter 14 may be in the range of about 60 to 150 cm, or about 80 to 120 cm, or about 100 to 115 cm, or about 112±0.02 cm. In some embodiments, the inner catheter 14 may have one or more sections with a differing hardness/stiffness (e.g., differing shore durometer). For example, the inner catheter 14 may have a proximal region and an intermediate region. In some embodiments, the proximal region may include a generally stiff polymeric material such as a 72D polyether block amide (e.g., 72D PEBAX) and may have a length in the range of about 60 to 150 cm, or about 80 to 120 cm, or about 100 to 115 cm, or about 109.5±0.02 cm. In some embodiments, the intermediate region may include a 40D polyether block amide (e.g., 40D PEBAX) and may have a length in the range of about 5 to 25 mm, or about 10 to 20 mm, or about 15±0.01 mm. The decreased outer diameter section may also differ from the proximal region and/or the intermediate region and, in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples.

In some embodiments, disposed within one of the lumens (e.g., a first lumen) of the inner catheter 14 may be at least one actuator element 84 (not shown in FIGS. 2B and 2C), which may be used to actuate (e.g., translate axially or longitudinally, and/or expand) the medical implant 16 between a delivery configuration and a deployed configuration. In some cases, the actuator element(s) 84 may herein be referred to, or used interchangeably with, the term "actuator element". In some embodiments, the medical device system 10 may include at least one actuator element 84. In some embodiments, the at least one actuator element 84 may include a plurality of actuator elements 84, two actuator elements 84, three actuator elements 84, four actuator elements 84, or another suitable or desired number of actuator elements 84. For the purpose of illustration only, the medical device system 10 and/or the medical implant 16 is shown with three actuator elements 84.

In at least some embodiments, the first lumen 46 may be lined with a low friction liner 54 (e.g., a FEP liner). In some embodiments, disposed within the second lumen 48 may be at least one release pin (not shown in FIGS. 2B and 2C), although dedicated release pins are not strictly necessary in every embodiment. In at least some embodiments, the second lumen 48 may be lined with a hypotube liner 56. The third lumen 50 may be a guidewire lumen and in some embodiments, the third lumen 50 may also be lined with a hypotube liner 59. In some embodiments, the fourth lumen 52 may be used to house a non-stretch wire or other reinforcing member 60. The form of the non-stretch wire or other reinforcing member 60 may vary. In some embodiments, the non-stretch wire 60 may take the form of a stainless steel braid. The non-stretch wire 60 may optionally include a pair of longitudinally-extending aramid and/or para aramid strands (for example, KEVLAR®) disposed on opposite sides of the braid. In general, rather than being "disposed within" the fourth lumen 52, the non-stretch wire may be embedded within the fourth lumen. In addition, the non-stretch wire may extend to a position adjacent to a distal end region but not fully to the distal end of the inner catheter 14. For example, a short distal segment of the fourth lumen may be filled in with polymer material adjacent to the distal end of the inner catheter 14.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element", "the locking element", "the lumen", or other features may be equally referred to all instances and quantities beyond one of said feature. As such, it will be understood that the following discussion may apply equally to any and/or all of the components for which there are more than one within the medical implant 16 (e.g., the at least one actuator element 84, the plurality of locking elements 76, the plurality of fingers 58, etc.) and/or the medical device system 10, unless explicitly stated to the contrary. Additionally, not all instances of some elements or features may be shown in each figure for clarity.

FIG. 3 illustrates some selected components of the medical device system 10 and/or the medical implant 16. For example, here it can be seen that the medical implant 16 may include a plurality of valve leaflets 68 (e.g., bovine pericardial, polymeric, etc.) which may be secured to a braided anchor member 70 at a post or commissure post 72, for example at the commissure portions of the leaflets 68. The braided anchor member may be reversibly actuatable between an elongated "delivery" configuration and an expanded "deployed" configuration. In some embodiments, the braided anchor member 70 may form a tubular structure defining a central longitudinal axis. In some embodiments, the medical implant 16 may include a plurality of locking elements 76 attached to the braided anchor member 70, the plurality of locking elements 76 being configured to lock the braided anchor member 70 in the "deployed" and/or "released" configuration(s). In some embodiments, at least one actuator element 84 may be configured to actuate the braided anchor member 70 and/or the medical implant 16 between the "delivery" configuration and the "deployed" configuration and/or the "released" configuration.

In some embodiments, the plurality of locking elements 76 may each comprise a post member, for example at the commissure portions of the valve leaflets 68 (the post member may sometimes be referred to as a portion of a commissure post, which may serve to secure the valve leaflets 68, or the post member may be connected and/or attached to a commissure post), and a buckle member or other receiving element configured to slidably receive the post member therein. In other words, in at least some embodiments, a medical implant 16 may include a plurality of post members and a corresponding a plurality of buckle members. Other configurations and correspondences are also contemplated. In some embodiments, the valve leaflets 68 may also be secured to a base or distal end of the braided anchor member 70. The post members and/or the commissure posts, in turn, may be secured and/or attached to the braided anchor member 70 (e.g., along the interior of the braided anchor member) with sutures, adhesives, or other suitable mechanisms. In some embodiments, the commissure post and/or the post member may include one or more holes or other features provided to aid in securing and/or attaching the commissure post and/or the post member to the braided anchor member 70. Positioned adjacent to (e.g., aligned with) the plurality of post members are a corresponding plurality of buckle members, which may be secured and/or fixedly attached to the braided anchor member 70 (e.g., along the interior of the braided anchor member 70) with sutures, adhesives, or other suitable mechanisms. In some embodiments, the post member may be axially translatable relative to the buckle member generally parallel to the central longitudinal axis of the braided anchor member 70 when the post member is at least partially disposed within and/or engaged with the buckle member.

In some embodiments, one buckle member may be fixedly attached to the braided anchor member 70 adjacent to each of the three post members. Accordingly, in some embodiments, the braided anchor member 70 may have a total of three buckle members and three post members attached thereto. Similarly, one actuator element 84 may be associated with each post member and buckle member, for a total of three actuator elements 84 in the illustrated example(s). Other embodiments are contemplated where fewer or more buckle members, post members, and/or actuator elements 84 may be utilized. In some embodiments, a seal 74 (shown in partial cross-section in FIG. 3) may be disposed on and/or about the braided anchor member 70 and may help to seal the medical implant 16 within a target site or area of interest upon deployment.

In at least some embodiments, the buckle member may be configured to slidably receive at least a portion of the post member within the longitudinal channel. In some embodiments, the buckle member may include one or more holes or other features provided to aid in attaching the buckle member to the braided anchor member 70. In some embodiments, the buckle member may be configured to engage with and/or lock the post member in the "deployed" configuration, such that distal axial translation of the post member relative to the buckle member is prevented. Some suitable but non-limiting materials for the buckle member and/or the post member, for example metallic materials or polymeric materials, may be described below.

Figure 4:
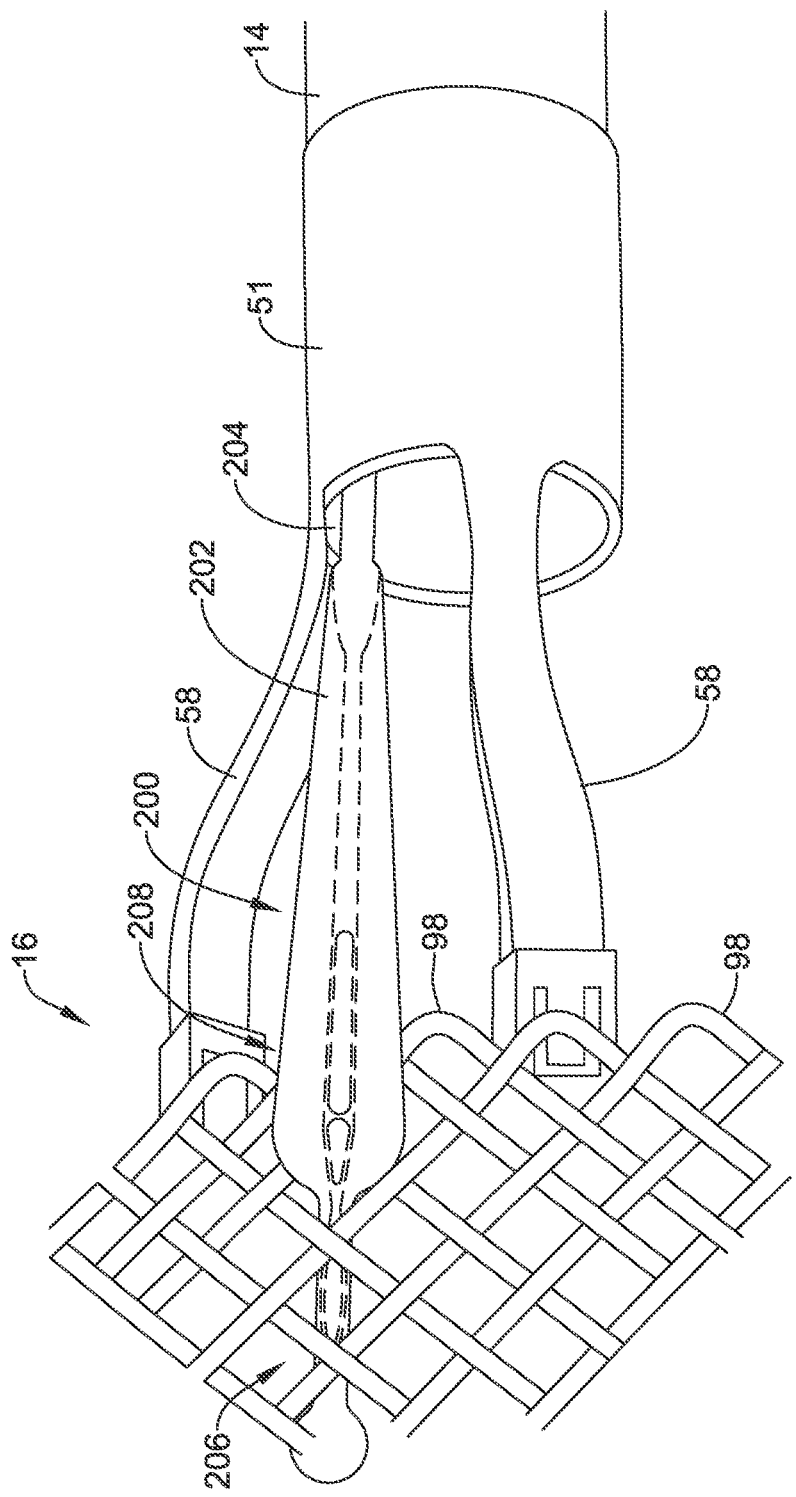
FIG. 4 illustrates selected components of an example medical device system.

In some embodiments, attachment between the medical implant 16 and the inner catheter 14 and/or the delivery system may be effected through the use of a coupler assembly 78, as seen in FIG. 3 for example. In at least some embodiments, the coupler assembly 78 may generally include a coupler ring 51, as shown in FIG. 4, disposed about and/or fixedly attached to the decreased diameter section 42 and/or at a distal end of the inner catheter 14. In some embodiments, the coupler assembly 78 may include a plurality of fingers 58 extending distally from the coupler ring 51. In some embodiments, the coupler assembly 78 may extend distally from the inner catheter 14. In some embodiments, each of the plurality of fingers 58 may be releasably coupled to one locking element 76 of the medical implant 16. As such, the medical implant 16 may include a plurality of locking elements 76 corresponding to the plurality of fingers 58. A collar 80 may further assist in holding together these structures. A guide 82 may be disposed over each of the fingers 58 and may serve to keep the plurality of fingers 58 of the coupler assembly 78 associated with the at least one actuator element 84 extending adjacent to the coupler assembly 78.

In some embodiments, an example actuator element 84 may include a proximal end and a distal end. In use, the proximal end may be connected to the handle 18, and/or manipulated or otherwise actuated by a user using the handle 18, to shift the braided anchor member 70 and/or the medical implant 16 from a "delivery" configuration to a "deployed" configuration, and later to a "released" configuration. In some embodiments, the actuator element 84 may include an elongated rod and a distal end portion. In some embodiments, the actuator element 84 and/or the distal end portion may be releasably connected to and/or coupled to the locking element 76. In some embodiments, the distal end portion may be integrally formed with or as a part of the elongated rod as a single monolithic structure. In some embodiments, the actuator element 84 may be prevented from rotating (e.g., is non-rotatable) relative to the locking element 76 when the actuator element 84 is engaged with the locking element 76. In some embodiments, after shifting the braided anchor member 70 and/or the medical implant 16 from the "delivery" configuration to the "deployed" configuration, continued proximal retraction, withdrawal, and/or translation of the at least one actuator element 84 may shift the braided anchor member 70 and/or the medical implant 16 from the "deployed" configuration to the "released" configuration. When shifting the braided anchor member 70 and/or the medical implant 16 from the "deployed" configuration to the "released" configuration, the distal end portion of the at least one actuator element 84 may engage with the collar 80, thereby retracting, withdrawing, and/or translating proximally the collar 80 relative to the locking element 76 to release the braided anchor member 70 and/or the medical implant 16.

In some embodiments, the actuator element 84 and/or the elongated rod may be generally round, oblong, ovoid, rectangular, polygonal (e.g., two-sided, three-sided, four-sided, five-sided, six-sided, etc.) and/or combinations thereof in shape. Other shapes, both regular and irregular, are also contemplated. In some embodiments, the actuator element 84 may be formed from a single piece of wire, round stock, or other suitable material, as discussed herein. In some embodiments, the actuator element 84 may be formed by further processing the single piece of wire, round stock, or other suitable material, such as by machining, stamping, laser cutting, etc. Some suitable but non-limiting materials for the actuator element 84, the elongated rod, and/or the distal end portion, for example metallic materials or polymeric materials, may be described below.

FIG. 4 illustrates another component that may be included with system 10. In some embodiments, a sheathing aid 200 may extend between and/or connect the delivery system to the medical implant 16. In some embodiments, the sheathing aid 200 may be configured to guide the medical implant 16 into the outer sheath 12 upon relative closing movement therebetween, as will be described in more detail below. In some embodiments, the sheathing aid 200 may include a plurality of arms 202 (e.g. a plurality of posts, a plurality of tines, a plurality of legs, a plurality of sheathing members, a plurality of segments, etc., which terms may be used interchangeably with a plurality of arms herein) extending distally from the inner catheter 14 to a proximal end of the braided anchor member 70 of the medical implant 16. In use, an arm 202 may be positioned between each of the fingers of coupler assembly 78. Because the coupler assembly 78 may have a total of three fingers, the sheathing aid 200 may have a total of three arms. However, this is just an example, the sheathing aid 200 may have fewer than three arms or more than three arms, as desired.

Each arm 202 may have a proximal portion 204 affixed to or otherwise secured relative to the inner catheter 14, a distal portion 206 configured to be woven into the braided anchor member 70, and an intermediate region 208 disposed therebetween. The intermediate region 208 may be configured to be disposed over the proximal end or crowns 98 of the braided anchor member 70 to facilitate sheathing or retraction of the braided anchor member 70 into the outer sheath 12. The intermediate region 208 may allow a percentage of the crowns 98 to be covered by the sheathing aid 200. This may reduce and/or prevent the crowns 98 from catching on the outer sheath 12 during sheathing of the braided anchor member 70 which may also reduce and/or eliminate the need for manual manipulation (e.g. user intervention) when loading the braided anchor member 70.

Figure 5:
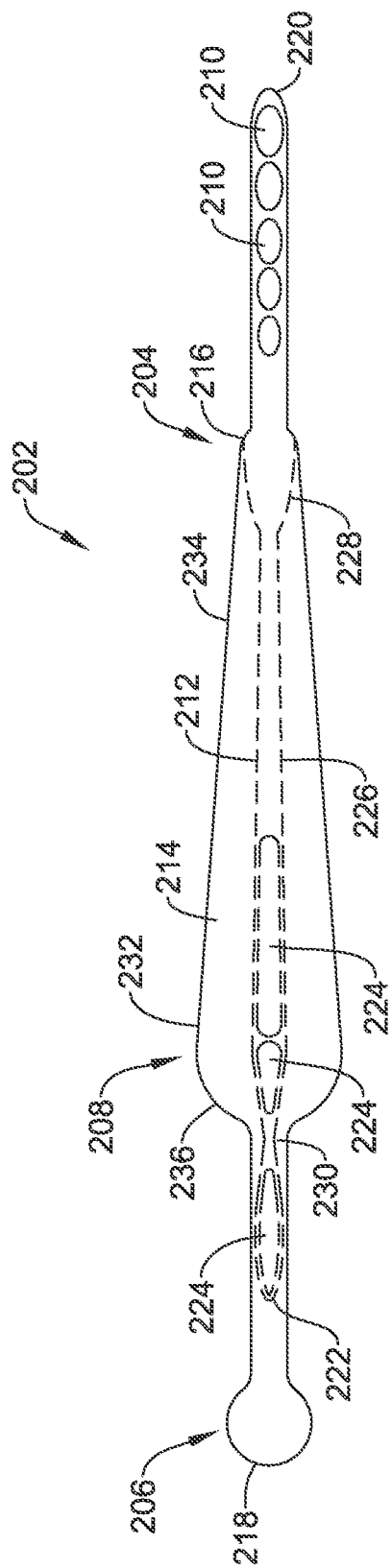
FIGS. 5-7 illustrate example arms of a sheathing aid of an example medical device system.

Referring additionally to FIG. 5, which illustrates an exemplary arm 202, in some embodiments, the proximal portion 204 of the arm 202 may include one or more apertures 210. These apertures 210 may facilitate attachment of the arms 202 to the inner catheter 14 through techniques such as, but not limited to, reflow, over molding, adhesives, etc.

Each arm 202 may include a core member 212 and a flexible member 214. The flexible member 214 may be positioned about, over and/or generally surround all or a portion of the core member 212. In some embodiments, at least a portion of the core member 212 may be fully embedded within the flexible member 214. In other embodiments, at least a portion of the core member 212 may be only partially embedded in the flexible member 214. For example, a portion of the core member 212 may extend from one or more surfaces of the flexible member 214. The flexible member 214 may extend from a proximal end 216 to a distal end 218. In some embodiments, the proximal end 216 of the flexible member 214 may be positioned distal to a proximal end 220 of the core member 212. For example, the proximal end 220 of the core member 212 may be configured to engage the inner catheter 14. In other embodiments, the proximal end 216 of the flexible member 214 may extend to the proximal end 220 of the core member 212 or beyond the proximal end 220 of the core member 212. The distal end 218 of the flexible member 214 may extend distally beyond a distal end 222 of the core member 212, although this is not required. In some embodiments, the distal end 218 of the flexible member 214 may be adjacent to the distal end 222 of the core member 212 or may be positioned proximal to the distal end 222 of the core member 212.

The core member 212 may be formed from a metallic, polymeric, or other material, having sufficient rigidity to apply a biasing force on the medical implant 16 as it is guided into the outer sheath 12. In some instances, the apertures 210 may be formed in the core member 212 adjacent the proximal end 220 thereof. The core member 212 may include one or more apertures 224 positioned adjacent the distal end 222 and/or intermediate region 226 of the core member 212. It is contemplated that the apertures 224 may facilitate attachment of the flexible member 214 and/or reduce the profile of the arm 202. The apertures 224 may vary in shape, size, and/or location, as desired. It is further contemplated that reducing the profile of the core member 212 may also reduce the stiffness of the system 10 to facilitate delivery of the braided anchor member 70.

The width of the core member 212 may vary along a longitudinal length thereof. For example, the core member 212 member may have a first width adjacent the proximal end 220, a second width adjacent the intermediate region 226, and a third width adjacent the distal end 222. However, the core member 212 is not limited to three distinct widths. For example, the core member 212 may include tapered and/or flared regions 228, 230 to gradually transition between widths. It is further contemplated that in some embodiments, the core member 212 may have fewer than three different widths or greater than three different widths, as desired. In some instances, the width of the core member 212 may remain constant, or substantially constant along a longitudinal length thereof.

The flexible member 214 may formed from a flexible polymeric material, such as, but not limited to, polyether ether ketone (PEEK). The flexible member 214 may be overmolded onto the core member 212, although other manufacturing techniques may also be used. For example, the flexible member 214 may be snap fit over the core member 212. The width of the flexible member 214 may vary along a longitudinal length thereof. For example, the flexible member 214 member may have a first width adjacent the proximal end 216, a second width adjacent the intermediate region 232, and a third width adjacent the distal end 218. However, the flexible member 214 is not limited to three distinct widths. For example, the flexible member 214 may include tapered and/or flared regions 234, 236 to gradually transition between widths. It is further contemplated that in some embodiments, the flexible member 214 may have fewer than three different widths or greater than three different widths, as desired. In some instances, the width of the flexible member 214 may remain constant, or substantially constant along a longitudinal length thereof.

In one illustrative example, the flexible member 214 may have a shape which flares, or gradually increases in width, from the proximal end 216 to the intermediate region 232. The intermediate region 232 may have an enlarged bulbous shape which tapers to a smaller width towards the distal end 218 of the flexible member 214. In some embodiments, the distal end 218 may be rounded or slightly enlarged to facilitate engagement of the arm 202 with the braided anchor member 70. This is just an example. The flexible member 214 and/or the core member 212 may take any shape desired.

The intermediate region 232 of the flexible member 214 may be have a width greater than the core member 212 and/or the remainder of the flexible member 214. The intermediate region 232 of the flexible member 214 may be disposed along the exterior of braid 70 acting as a funnel for sheathing. The increased width of the intermediate region may allow a larger percentage of the crowns 98 to be covered by the sheathing aid 200. This may reduce and/or prevent the crowns 98 from catching on the outer sheath 12 during sheathing of the braided anchor member 70 which may also reduce and/or eliminate the need for manual manipulation (e.g. user intervention) when loading the braided anchor member 70.

While the intermediate region 232 of the flexible member may be disposed on an outer surface of the braided anchor member 70, the distal end region 206 including the distal end 218 of the flexible member 214 may be woven into the braided anchor member 70, such that the distal end 218 of the flexible member 214 may be disposed within the lumen, or along an inner surface, of the braided anchor member 70. The arms 202 may remain engaged with the braided anchor member 70 during the "deployment" of the braided anchor member 70 to facilitate re-sheathing the braided anchor member 70 if so desired. When the braided anchor member 70 is positioned in the desired location, the actuator element 84 may be manipulated, as described above to release the braided anchor member 70. The arms 202 may be disengaged from the braided anchor member 70 through proximal retraction of the inner catheter 14 to complete the transition of the medical implant 16 from the "deployed" configuration to the "released" configuration. The inner catheter 14 and/or the coupler assembly 78 may be re-sheathed within the outer sheath 12 via relative translation therebetween (e.g., advancing the outer sheath 12 distally over the inner catheter 14 and/or the coupler assembly 78, withdrawing the inner catheter 14 and/or the coupler assembly 78 proximally within the outer sheath 12, a combination thereof, etc.). Thereafter, the delivery system may be withdrawn and/or removed from the anatomy, leaving behind the expanded and deployed medical implant 16 disposed at the target site in a "released" configuration.

Figure 6:
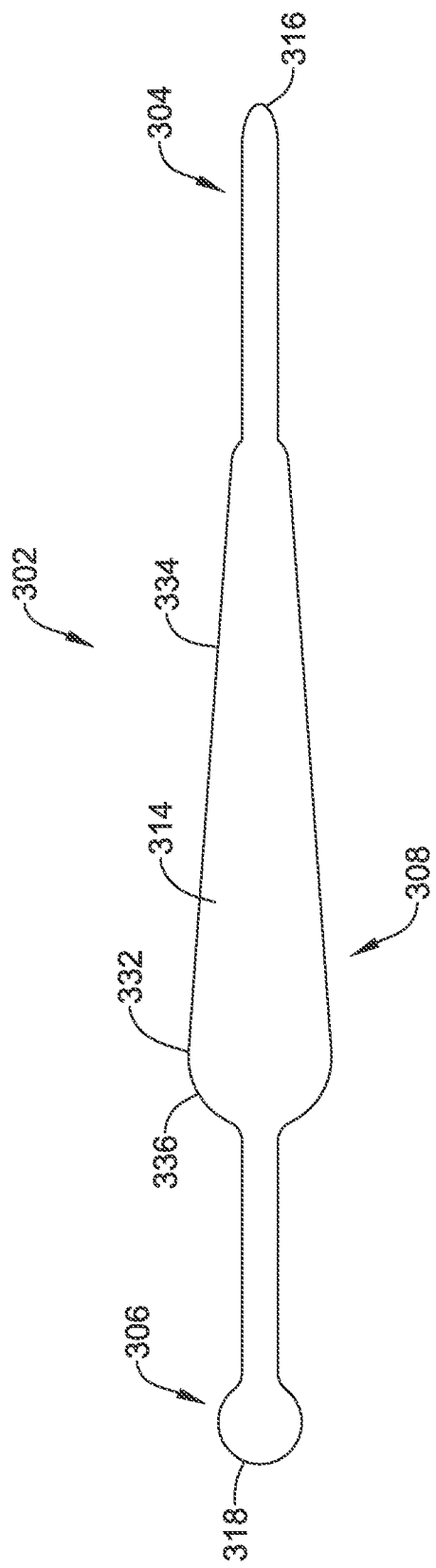

FIG. 6 illustrates another example arm 302 for use with a sheathing mechanism 200. The arm 302 may be similar in form and function to the arm 202 described above with respect to FIG. 5. However, arm 302 may be formed solely from a flexible member 314. Each arm 302 may have a proximal portion 304 affixed to or otherwise secured relative to the inner catheter 14, a distal portion 306 configured to be woven into the braided anchor member 70, and an intermediate region 308 disposed therebetween. The arms 302 may be attached to the inner catheter 14 through techniques such as, but not limited to, reflow, overmolding, heat welding, adhesives, etc.

The flexible member 314 may formed from a flexible polymeric material, such as, but not limited to, polyether ether ketone (PEEK). The flexible member 314 may be molded into the desired shape, although other manufacturing techniques may also be used. The width of the flexible member 314 may vary along a longitudinal length thereof. For example, the flexible member 314 member may have a first width adjacent the proximal end 316, a second width adjacent the intermediate region 332, and a third width adjacent the distal end 318. However, the flexible member 314 is not limited to three distinct widths. For example, the flexible member 314 may include tapered and/or flared regions 334, 336 to gradually transition between widths. It is further contemplated that in some embodiments, the flexible member 314 may have fewer than three different widths or greater than three different widths, as desired. In some instances, the width of the flexible member 314 may remain constant, or substantially constant along a longitudinal length thereof.

In one illustrative example, the flexible member 314 may have a shape which flares, or gradually increases in width, from the proximal end 316 to the intermediate region 332. The intermediate region 332 may have an enlarged bulbous shape which tapers to a smaller width towards the distal end 318 of the flexible member 314. In some embodiments, the distal end 318 may be rounded or slightly enlarged to facilitate engagement of the arm 302 with the braided anchor member 70. This is just an example. The flexible member 314 may take any shape desired.

The intermediate region 332 of the flexible member 314 may be disposed along the exterior of braid 70 acting as a funnel for sheathing. The increased width of the intermediate region may allow a larger percentage of the crowns 98 to be covered by the sheathing aid 200. This may reduce and/or prevent the crowns 98 from catching on the outer sheath 12 during sheathing of the braided anchor member 70 which may also reduce and/or eliminate the need for manual manipulation (e.g. user intervention) when loading the braided anchor member 70.

While the intermediate region 332 of the flexible member 314 may be disposed on an outer surface of the braided anchor member 70, the distal end region 306 including the distal end 318 of the flexible member 314 may be woven into the braided anchor member 70, such that the distal end 318 of the flexible member 314 may be disposed within the lumen, or along an inner surface, of the braided anchor member 70. The arms 302 may remain engaged with the braided anchor member 70 during the "deployment" of the braided anchor member 70 to facilitate re-sheathing the braided anchor member 70 if so desired. When the braided anchor member 70 is positioned in the desired location, the actuator element 84 may be manipulated, as described above to release the braided anchor member 70. The arms 302 may be disengaged from the braided anchor member 70 through proximal retraction of the inner catheter 14 to complete the transition of the medical implant 16 from the "deployed" configuration to the "released" configuration. The inner catheter 14 and/or the coupler assembly 78 may be re-sheathed within the outer sheath 12 via relative translation therebetween (e.g., advancing the outer sheath 12 distally over the inner catheter 14 and/or the coupler assembly 78, withdrawing the inner catheter 14 and/or the coupler assembly 78 proximally within the outer sheath 12, a combination thereof, etc.). Thereafter, the delivery system may be withdrawn and/or removed from the anatomy, leaving behind the expanded and deployed medical implant 16 disposed at the target site in a "released" configuration.

Figure 7:
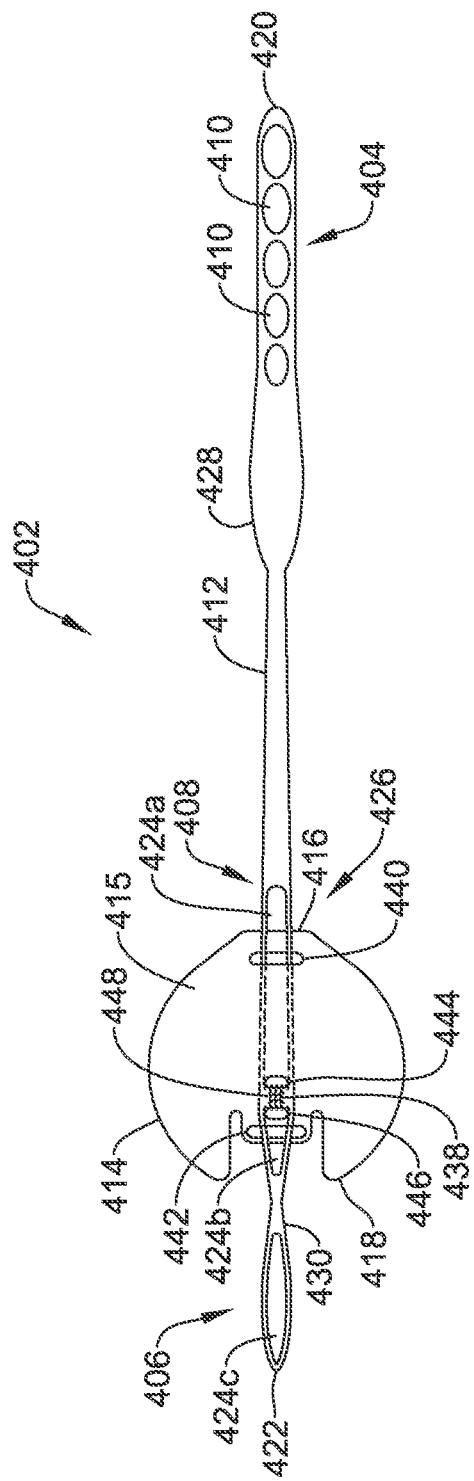

FIG. 7 illustrates another example arm 402 for use with a sheathing mechanism 200. The arm 402 may be similar in form and/or function to the arms 202, 302 described above with respect to FIGS. 5 and 6. Each arm 402 may have a proximal portion 404 affixed to or otherwise secured relative to the inner catheter 14, a distal portion 406 configured to be woven into the braided anchor member 70, and an intermediate region 408 disposed therebetween. In some embodiments, the proximal portion 404 of the arm may include one or more apertures 410. These apertures 410 may facilitate attachment of the arms 402 to the inner catheter 14 through techniques such as, but not limited to, reflow, overmolding, etc.

Each arm 402 may include a core member 412 and a flexible member 414. The flexible member 414 may be generally positioned over a portion of the core member 412. In some embodiments, the flexible member 414 may be removably secured to the core member 412 through such techniques as suturing 438, as will be discussed in more detail below. In other embodiments, the flexible member 414 may be overmolded on the core member 412. These are just examples. The flexible member 414 may be releasably or fixedly secured to the core member 412 using any method desired.

The core member 412 may be formed from a metallic, polymeric, or other material, having sufficient rigidity to apply a biasing force on the medical implant 16 as it is guided into the outer sheath 12. As described above, the core member 412 may include one or more apertures 410 adjacent the proximal end 420 thereof. The core member 412 may include one or apertures 424a, 424b, 424c (collectively 424) positioned adjacent the distal end 422 of the core member 412 and/or an intermediate region 426 of the core member 412. It is contemplated that the apertures 424 may facilitate attachment of the flexible member 414 and/or reduce the profile of the arm 402. In some instances, apertures 424 may be sized and shaped to allow the flexible member to be sutured 438 to the core member 412. The apertures 424 may vary in shape, size, and/or location, as desired. It is further contemplated that reducing the profile of the core member 412 may also reduce the stiffness of the system 10 to facilitate delivery of the braided anchor member 70. The width of the core member 412 may vary along a longitudinal length thereof.

For example, the core member 412 member may have a first width adjacent the proximal end 420, a second width adjacent the intermediate region 426, and a third width adjacent the distal end 422. However, the core member 412 is not limited to three distinct widths. For example, the core member 412 may include tapered and/or flared regions 428, 430 to gradually transition between widths. It is further contemplated that in some embodiments, the core member 412 may have fewer than three different widths or greater than three different widths, as desired. In some instances, the width of the core member 412 may remain constant, or substantially constant along a longitudinal length thereof. The core member 412 may take any shape and/or size desired.

The flexible member 414 may be a generally round pad or paddle 415 configured to be disposed adjacent to the intermediate region 426 of the core member 412. However, the pad 415 may take any shape desired, such as, but not limited to square, rectangular, ovular, polygonal, eccentric, etc. The flexible member 414 may formed from a flexible polymeric material, such as, but not limited to, polyether ether ketone (PEEK). The flexible member 414 may be overmolded onto the core member 412, although other manufacturing techniques may also be used. For example, the flexible member 414 may be snap fit over the core member 412 or secured via an adhesive. In other embodiments, the flexible member 414 may be sutured 438 to the core member 412. Referring additionally to FIG. 8, the pad 415 may include a first aperture 440 positioned adjacent to a proximal end 416 of the pad 415 and a second aperture 442 positioned adjacent to a distal end 418 of the pad 415. The first and second apertures 440, 442 may have a width that is similar to or slight larger than the widest portion of the distal end 422 (or in some instances, the proximal end 420) of the core member 412.

To couple the core member 412 and the flexible member 414, the distal end 422 of the core member 412 may be slid through the first aperture 440. While FIG. 7 illustrates the core member 412 as entering the aperture 440 from the top surface of the flexible member 414, it is contemplated that core member 412 may alternatively enter the aperture 440 from the back surface of the flexible member 414. The distal end 422 of the core member 412 may then be slid through the second aperture 442. It is contemplated that the distal end 422 may be slid through the second aperture 442 from an opposite side as it was slid through the first aperture 440. For example, if the distal end is advanced through the first aperture 440 from the front side to the back side of the flexible member 414, the distal end may be advanced through the second aperture from the back side to the front side of the flexible member 414 such that the flexible pad 414 is "woven" onto the core member 412. The flexible member 414 may further include a third aperture 444 and a fourth aperture 446. The third aperture 444 of the flexible member 414 may be generally aligned with a first aperture in the core member 412 and the fourth aperture 446 of the flexible member 414 may be generally aligned with a second aperture 424b in the core member 412. A bridge 448 may be positioned between the first and second apertures 424a, 424b of the core member 412 such that sutures 438 may pass through the first and second apertures 424a, 424b of the core member 412 and the third and fourth apertures 444, 446 of the flexible member 414 to secure the flexible member 414 to the core member 412.

In some embodiments, the distal end 418 of the flexible member 414 may include one or more valleys 449 and one or more peaks 450. The valleys 449 and/or peaks 450 may be engage a portion of the braided anchor member 70 to maintain the flexible member 414 in a desired configuration. For example, the peaks 450 and/or the distal end 422 of the core member 422 may be woven into the braided anchor member 70 such that the peaks 450 and/or the distal end 422 of the core member 422 are disposed along an inner surface of the braided anchor member 70. The remaining portion of the pad 415 may be disposed along the exterior of braid 70 acting as a funnel for sheathing. The width of the pad 415 may allow a larger percentage of the crowns 98 to be covered by the sheathing aid 200. This may reduce and/or prevent the crowns 98 from catching on the outer sheath 12 during sheathing of the braided anchor member 70 which may also reduce and/or eliminate the need for manual manipulation (e.g. user intervention) when loading the braided anchor member 70.

The arms 402 may remain engaged with the braided anchor member 70 during the "deployment" of the braided anchor member 70 to facilitate re-sheathing the braided anchor member 70 if so desired. When the braided anchor member 70 is positioned in the desired location, the actuator element 84 may be manipulated, as described above to release the braided anchor member 70. The arms 402 may be disengaged from the braided anchor member 70 through proximal retraction of the inner catheter 14 to complete the transition of the medical implant 16 from the "deployed" configuration to the "released" configuration. The inner catheter 14 and/or the coupler assembly 78 may be re-sheathed within the outer sheath 12 via relative translation therebetween (e.g., advancing the outer sheath 12 distally over the inner catheter 14 and/or the coupler assembly 78, withdrawing the inner catheter 14 and/or the coupler assembly 78 proximally within the outer sheath 12, a combination thereof, etc.). Thereafter, the delivery system may be withdrawn and/or removed from the anatomy, leaving behind the expanded and deployed medical implant 16 disposed at the target site in a "released" configuration.

FIGS. 9 and 10 illustrate partial cutaway segments of the example sheathing aid 200 including a plurality of arms 202 extending from the inner catheter 14 and/or the coupler ring 51 to a proximal end of the braided anchor member 70 and/or the medical implant 16. While the sheathing aid 200 is described as including arms 202, it should be understood that any of the other arms 302, 402 described herein may be used in place of or in combination with arms 202. FIG. 9 illustrates a portion of the medical device system 10 in an "unsheathed" or "deployed" configuration. As the inner catheter 14 and/or the medical implant 16 is retracted, withdrawn, and/or translated proximally relative to the outer sheath 12 (and/or the outer sheath 12 is advanced distally relative to the inner catheter 14 and/or the medical implant 16), the plurality of arms 202 may contact a distal end of the outer sheath 12. In some embodiments, the plurality of arms may act as levers against the distal end of the outer sheath 12 to provide a mechanical advantage for collapsing the braided anchor member 70 toward the "sheathed" or "delivery" configuration. FIG. 10 illustrates a portion of the medical device system 10 in a partially-sheathed configuration wherein the proximal end of the braided anchor member 70 and/or the medical implant 16 has begun to collapse.

Due to the attachment and/or positioning of the plurality of arms 202 and/or the plurality of fingers 58 to and/or over many and/or all of the crowns 98 of the braided anchor member 70, few or none of the crowns 98 may protrude radially outward to interfere with and/or catch or snag on the distal end of the outer sheath 12 during sheathing. Attaching and/or positioning the plurality of arms 202 and/or the plurality of fingers 58 to each and/or over many of the crowns 98 of the braided anchor member 70 may also distribute retraction and/or pulling forces among the crowns 98.

The materials that can be used for the various components of the medical device system 10 (and/or other systems disclosed herein) and the various elements thereof disclosed herein may include those commonly associated with medical devices. For simplicity purposes, the following discussion makes reference to the delivery system and/or the medical implant 16. However, this is not intended to limit the devices and methods described herein, as the discussion may be applied to other elements, members, components, or devices disclosed herein, such as, but not limited to, the braided anchor member 70, the actuator element 84, the sheathing aid 200, the coupler assembly 78, the post member, the buckle member, etc. and/or elements or components thereof.

In some embodiments, the medical device system 10, the delivery system, the sheathing aid 200, and/or the medical implant 16, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system, the sheathing aid 200, and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (Mill) compatibility is imparted into the medical device system 10. For example, the delivery system and/or the medical implant 16, and/or components or portions thereof, may be made of a material that does not substantially distort the image and create substantial artifacts (e.g., gaps in the image). Certain ferromagnetic materials, for example, may not be suitable because they may create artifacts in an Mill image. The delivery system and/or the medical implant 16, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device apparatus, comprising:
a medical implant including a braided anchor member, the braided anchor member operatively connected to a delivery system, the delivery system including a handle, an outer sheath extending distally from the handle, and an inner catheter disposed within the outer sheath; and
a sheathing aid connecting the inner catheter of the delivery system to the medical implant, the sheathing aid being configured to guide the medical implant into the outer sheath upon relative closing movement therebetween;
wherein the sheathing aid includes a plurality of arms extending from the inner catheter to an outer surface of a proximal end of the braided anchor member; and
wherein at least one arm of the plurality of arms comprises a metallic core member having a width and a flexible polymeric member extending along at least a portion of a length of the metallic core member and fixedly secured to the metallic core member, the flexible polymeric member comprising a proximal region, an enlarged intermediate region and a distal region,
wherein the plurality of arms extends over the outside surface at the proximal end of the braided anchor member and a distalmost end of each of the plurality of arms is disposed entirely within a lumen of the braided anchor member;
wherein the metallic core member is immovable relative to the flexible polymeric member.

2. The medical device apparatus of claim 1, wherein a distal end of the flexible polymeric member extends distally beyond a distal end of the metallic core member.

3. The medical device apparatus of claim 1, wherein the enlarged intermediate region of the flexible polymeric member has a width greater than the width of the metallic core member.

4. The medical device apparatus of claim 1, wherein the braided anchor member includes a plurality of crowns, wherein the enlarged intermediate region of the flexible polymeric member is configured to be disposed over at least one of the plurality of crowns.

5. The medical device apparatus of claim 1, wherein the width of the metallic core member varies along its length.

6. A medical device apparatus, comprising:
a medical implant including a braided anchor member, the braided anchor member operatively connected to a delivery system, the delivery system including a handle, an outer sheath extending distally from the handle, and an inner catheter disposed within the outer sheath; and
a sheathing aid connecting the inner catheter of the delivery system to the medical implant, the sheathing aid being configured to guide the medical implant into the outer sheath upon relative closing movement therebetween;
wherein the sheathing aid includes a plurality of arms extending from the inner catheter to engage an outer surface of the braided anchor member proximate a proximal end of the braided anchor member,
wherein an intermediate region of the flexible polymeric member is disposed at the proximal end of the braided anchor member against the outer surface of the braided anchor member, a distal end region of the flexible polymeric member distal of the intermediate region extends through the braided anchor member, and a distal end of the flexible polymeric member is disposed within a lumen of the braided anchor member; and
wherein at least one arm of the plurality of arms comprises a metallic core member having a width and a flexible polymeric member overmolded onto at least a portion of the metallic core member;
wherein the sheathing aid does not wrap around any portion of the braided anchor member.

7. The medical device apparatus of claim 6, wherein the braided anchor member includes a plurality of crowns, wherein the flexible polymeric member is configured to be disposed over at least one of the plurality of crowns.

* * * * *